Figure 1:
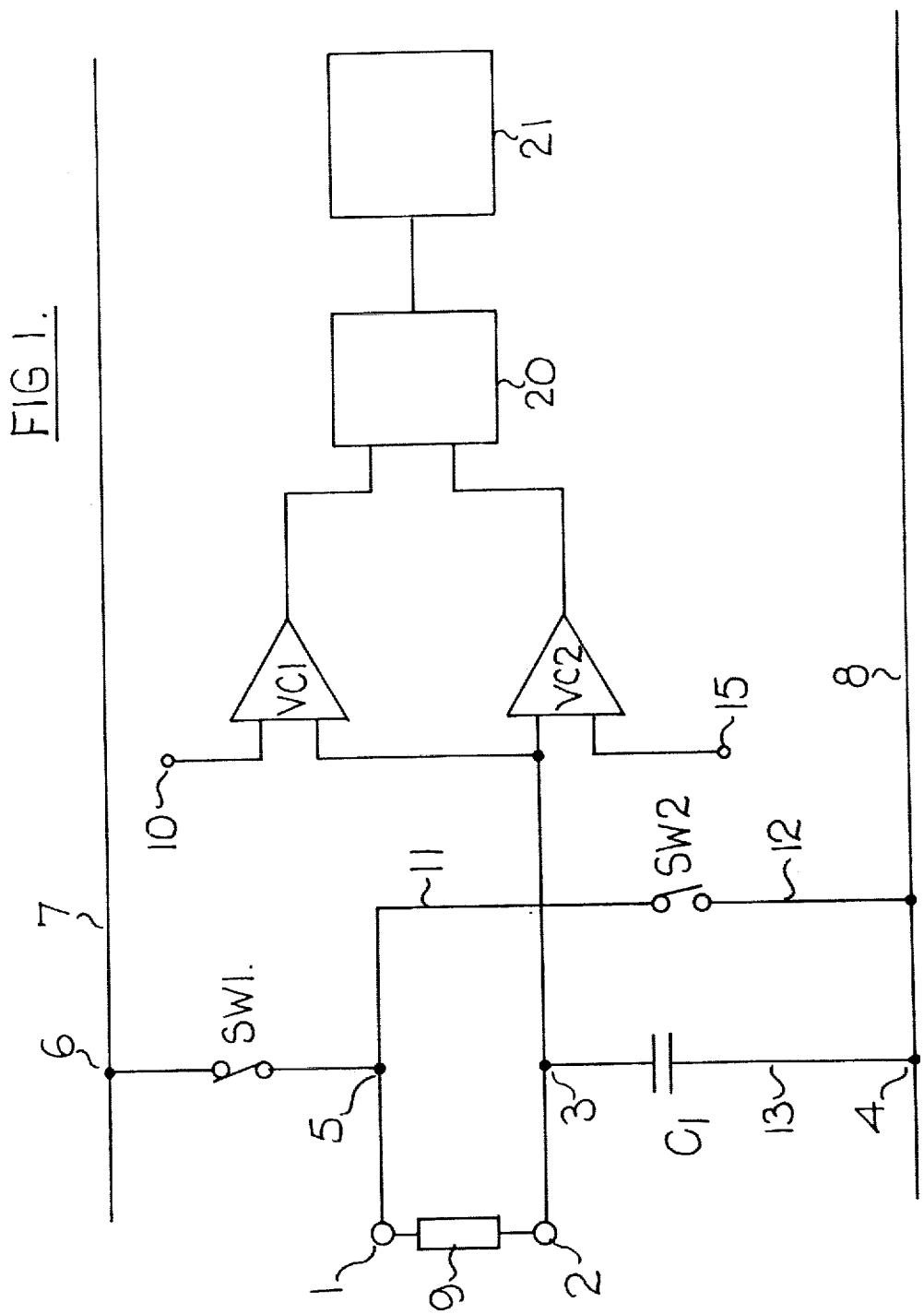

United States Patent [19]

Stephen

[11] 4,309,660
[45] Jan. 5, 1982

[54] METHODS AND APPARATUS FOR MEASURING ELECTRICAL CONDUCTIVITY

[75] Inventor: Stuart J. Stephen, Auckland, New Zealand

[73] Assignee: AHI Operations, Limited, Manukau City, Auckland, New Zealand

[21] Appl. No.: 205,240

[22] Filed: Nov. 10, 1980

Related U.S. Application Data

[63] Continuation of Ser. No. 000,982, Jan. 4, 1979, abandoned.

[30] Foreign Application Priority Data

Nov. 2, 1978 [NZ] New Zealand .................. 188810

[51] Int. Cl.³ .......................................... G01N 27/42
[52] U.S. Cl. ................................. 324/442; 324/439
[58] Field of Search ........................ 324/439, 442; 119/14.14; 331/65, 144

[56] References Cited

U.S. PATENT DOCUMENTS 4,160,946  7/1979  Frigate ........................... 324/442

Primary Examiner—Michael J. Tokar
Attorney, Agent, or Firm—Holman & Stern

[57] ABSTRACT

Methods and apparatus for measuring electrical conductivity particularly but not solely for use in detecting mastitis in individual quarters of a cow's udder employ the cyclical charge and discharge of a capacitor (C1) through liquid in a conductivity cell (9), the cycle reversing on the potential applied to the capacitor (C1) reading a high reference potential and a low reference potential by applying the reference potentials to terminals (10,15) or sensing leads (32,33) of electronic devices (VC1, VC2) or (31) to cause operation of switches (SW1, SW2) or (S1, S2) so that the variations in frequency are indications of conductivity of the cell (9). In one modification a reference conductance (30) is included in the circuit during charging of the capacitor (31) and the rate of the time periods of the cycle gives an indication of the conductance of the cell (9) in terms of the reference conductance (30).

3 Claims, 3 Drawing Figures

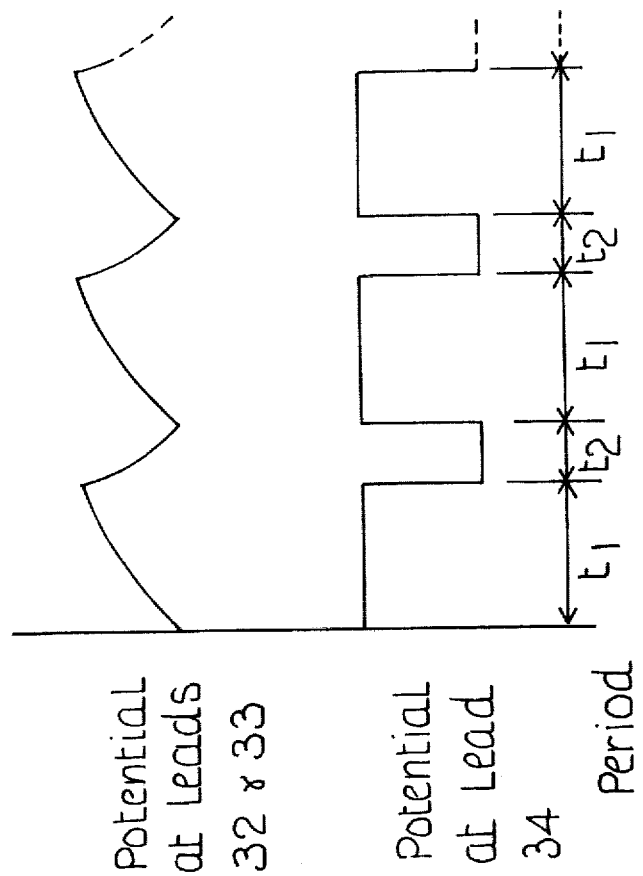

METHODS AND APPARATUS FOR MEASURING ELECTRICAL CONDUCTIVITY

This is a continuation of application Ser. No. 000,982, filed Jan. 4, 1979, and now abandoned.

This invention relates to methods of and/or apparatus for measuring electrical conductivity.

Methods of and/or apparatus for measuring electrical conductivity are known. In U.S. Pat. No. 3,664,306 a method and apparatus are described for detecting mastitis in milk animals. Milk from different teats of the animal is passed through conductivity cells and if the conductance of the milk from one teat is different from that of milk from other teats a mastitis infection is likely. A convenient method of comparing conductances using an electrical bridge is described, as is a suitable conductivity cell.

Such method and apparatus suffer from instability due to polarity effects and drift in accuracy due to the effects of temperature degradation of components over the life of the instrument and voltage variation. The invention as claimed is intended to provide a remedy or at least provide the public with a useful choice.

The advantages offered by the invention at least in the preferred form are:

1. The circuitry can be arranged to give very satisfactory accuracy in a very simple manner so that not only is the apparatus cheaper but also likely to be more accurate than present constructions.
2. Because of the simplicity of the circuitry little maintenance troubles are likely and the device should be capable of being used in the field by non-experienced persons.

Figure 2:
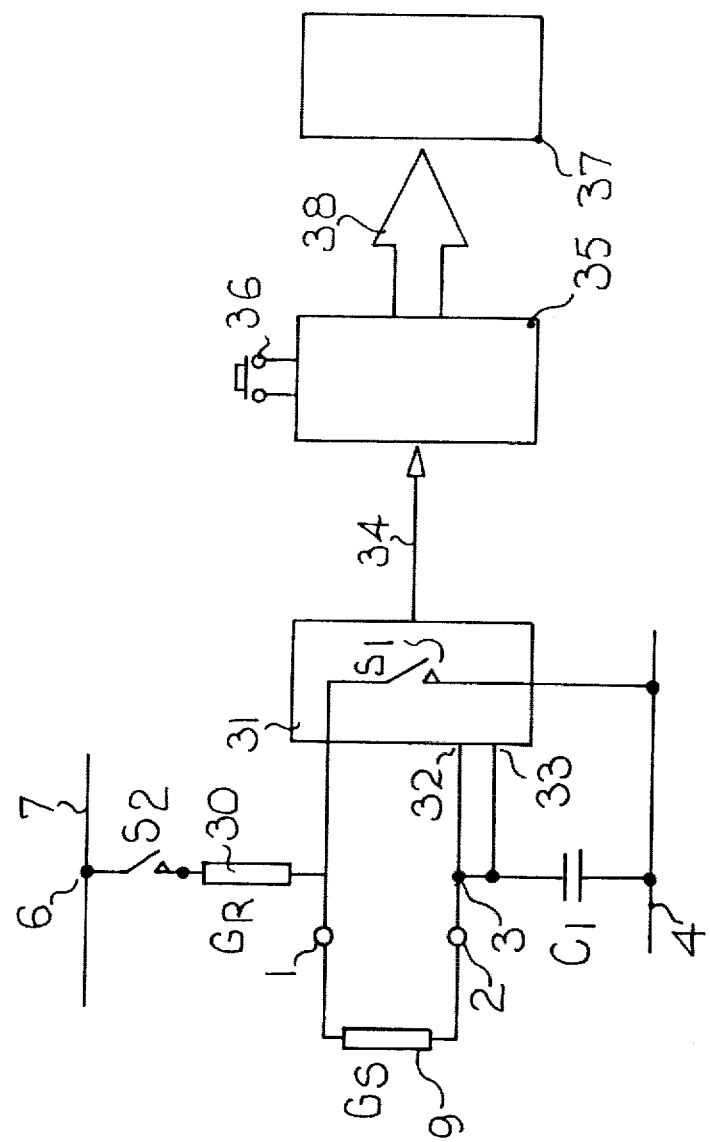

Ways of carrying out the invention are described in detail below with reference to drawings which illustrate specific embodiments and in which:

FIG. 1 is a block circuit diagram of one electronic circuit according to the invention, FIG. 2 is a diagrammatic representation of a modified circuit according to the invention, and FIG. 3 shows circuit potential waveforms produced in use by parts of the circuit shown in FIG. 2.

Referring to FIG. 1 of the drawings the invention includes the use of a conductivity to frequency converter and a micro-processor to process the data obtained from such converter and presented in preferably digital read-out form to the operator. Thus, an electrolytic cell 9 of any known type is connected to terminals 1 and 2 which will be referred to herein as the cell electrodes. One terminal of a capacitor C1 is connected at 3 to electrode 2, the other terminal of the capacitor being connected to a lead 4. A first switch SW1 is connected at 5 to electrode 1, the other terminal of SW1 being connected at 6 to an upper potential lead 7. A second switch SW2 has one terminal connected to electrode 1 and the other terminal connected to the lower potential lead 8.

The operation of this part of the circuit is as follows:

It will be assumed that a suitable potential is supplied between leads 7 and 8 and that a liquid is introduced into the conductivity cell so that there is a liquid, the conductivity of which is to be measured between electrodes 1 and 2. It will be assumed that the capacitor C1 has zero or low potential between terminal 2 and junction 4. As a result of the application of a potential from lead 7 through switch SW1 terminal 1, the liquid, terminal 2 and capacitor C1, capacitor C1 will ramp up exponentially until a voltage is reached corresponding to the upper reference voltage applied at terminal 10 to a suitable electronic device VC1. When this voltage is reached switches SW1 and SW2 are changed over from the closed position of SW1 and open position of SW2 to an open condition of SW1 and a closed condition of SW2. As a result the capacitor C1 will now discharge through the circuit comprising terminal 2, the liquid in the cell terminal 1, lead 11, switch SW2, lead 12, lead 8 or part of lead 8 and lead 13. This continues until a lower reference potential applied at 15 to electronic device VC2 is reached and when this occurs the condition of switches SW1 and SW2 will return to the condition shown in the drawings. The cycle of operations is then repeated. The time of variation of voltage, i.e. the cycle time, will be directly proportional to the conductivity of the sample. VC1 and VC2 have very low input biasing currents and their effect on the current flow through the conductivity cell can be ignored. It can be readily seen that the sum of the currents through the conductivity cell is substantially zero and that the output of the converter will be at a frequency of variation of potential proportional to the conductivity of the sample under test. The current through the electrolytic cell reverses in phase cyclically at a frequency proportional to the cell conductivity. In an actual application SW1 and SW2 would be bi-polar switches and VC1 and VC2 and switching logic would be part of an integrated timer such as an LM555. For the tight specification of an LM555 the following characteristics for a conductivity to frequency converter could be expected:

Drift with temperature: 0.009% frequency change/°C.

Drift with supply: 0.05%/Volt

Initial accuracy: 1.5%

By using regulated power supplies ovens and calibrating the converter it can be seen that a very high degree of accuracy is obtainable and many errors will be offset errors.

The output of the converter is changed into a binary format under program control by a micro-processor including circuit 20 under program control by the micro-processor so that data processing can be performed. The micro-processor is arranged to effect auto ranging and calibrating and calibrating can be effected automatically in the following manner.

Under program control a reference resistor is switched across the conductivity cell inputs at the same time as the cell is open-circuited. This occurs, for example, every ten seconds. The frequency of the converter is measured with the reference in circuit and any deviation from an ideal reference is used to update an internal conversion factor. This error correction technique may also be used to compensate for different conductivity cell constants. All an operator need do is to take any size or shape of cell, fill it with a reference conductivity solution, push a calibrate switch and the micro-processor would automatically adjust its conversion factors to compensate for the different cell constants.

The result of the data processing can be presented to a multi-digit display circuit 21 for reading by the operator. Alternatively, recording, for example, in the form of printouts can be provided by any known method.

Use of a single chip micro-processor such as National's COPS series enables a conductivity measurement system comprising perhaps three or four chips, a few discrete components and a multi-digit display may then be made at considerably less cost but far better performance than existing systems.

It is known that measurement of conductivity poses many problems when applied to electrolytes. The voltage applied to the sampling probes must undergo a phase reversal at regular intervals to reduce polarisation effects. The standard method of measuring conductivity is to make the conductivity cell one leg of a Wheatstone Bridge driven by AC and using nulling techniques to determine the conductivity of the samples electrolytic. The read-out presented to the operator is analog (such as panel mounted moving coil meters) in nature and thus suffers many disadvantages compared with digital circuitry such as limited accuracy, drift and poor repeatability. The technique that we propose should overcome these limitations plus offering additional features such as auto ranging and auto calibrating.

Referring now to FIGS. 2 and 3 of the drawings, the preferred form of the invention includes the use of a conductivity/time period converter and a micro-processor to analyse the data obtained from such a converter and to present any such information so obtained in a display unit, for example, a digital display unit. Thus, referring to FIG. 2 again an electrolytic conductivity cell of any known type is connected between terminals 1 and 2. When filled with an electrolyte whose conductivity is to be determined this cell will exhibit an electrical conductivity between its terminals hereinafter referred to as a conductivity of $G_s$.

Capacitor C1 is connected from terminal 2 of the cell to a power supply lead 4 and a conductive element 30 of conductivity $G_r$ is connected between terminal 1 of the cell and through an optional switch S2 at 6 to power supply lead 7 of differing potential from lead 4. A logic unit 31 (e.g. an LM555) includes a switch S1 to enable discharge of the capacitor C1 and in addition sensing leads 32 and 33 are provided to enable the state of charge of the capacitor to be monitored. An output lead 34 carries the measured conductivity information to a micro-processor (e.g. an 8048) unit 35 having a command switch 36, the micro-processor in turn feeding a display unit 37 through indicator 38, the display unit being preferably a digital display unit.

The operation of the above is as follows.

It will be assumed that a suitable potential nominated as $V_s$ is maintained between leads 7 and 4 and that a liquid has been introduced into the cell such that a conductivity $G_s$ is presented across terminals 1 and 2 as above referred to. It will be assumed that the capacitor C1 starts at a lower threshold of charge $V_1$ which may be determined by the sense leads 32 and 33 of the LM555 logic unit 31. Switch S1 is open and switch S2 if present is closed causing a charge to be passed through S2 and conductances $G_r$ and $G_s$ into C1. When the amount of charge in C1 reaches an upper limit $V_2$ sensed by the sensing leads 32 and 33 switch S2 is opened. The time taken to reach such a charge state is dependent on the series value of $G_r$ and $G_s$. Switch S1 is now closed. It will be seen that the capacitor will be discharged through the cell conductance $G_s$ in a reverse direction and when the remaining charge in the capacitor again reaches the initial value, S1 is opened completing a cycle. The time to perform the part of the cycle when switch S1 is closed is dependent on the value of $G_s$ and not $G_r$ as $G_r$ is disconnected at this time. In other words C1 and $G_s$ are short-circuited on each other. Thus, during the closed period of S1 no potential is maintained between terminal 1 and lead 4, thus allowing S2 to remain closed without materially affecting the operation of the circuit. Thus, switch S2 may be optional as was mentioned above.

The nett charge transfer through $G_s$ during the whole cycle is essentially zero. In detail it may be shown that the ratio of the time periods thus obtained may be made independent of certain circuit parameters and dependent to a first order on $G_r$ and $G_s$ only from which $G_s$ may be determined.

Thus it is assumed that the charge limits on the capacitor C1 are measured by monitoring the potential across such capacitor giving upper and lower voltage limits nominated $V_1$ and $V_2$ respectively.

It may be shown that for a series circuit comprising a capacitor of value C and a conductance G in series, connected to a potential $V_s$ that the voltage V across the capacitor is given by the form:

$$V = V_s(1 - e^{-(tG)/(c)})$$

from which it may be shown that by choosing suitable potentials for $V_s$, $V_1$ and $V_2$ that the time taken to charge or discharge the capacitor between limits $V_1$ and $V_2$ takes the form:

$$t = KC/G$$

where K is a constant value comprising logarithmic terms of potential, made equal for charge and discharge of the capacitor by suitable selection of potentials $V_s$, $V_1$ and $V_2$, as discussed above.

Specifically with reference to the drawing:

$$t_1 = \frac{K \cdot C_1}{G_{ser}} = K \cdot C_1 \frac{(G_r + G_s)}{G_r \cdot G_s} \text{ and}$$

$$t_2 = \frac{K \cdot C_1}{G_s} \text{ from which}$$

$$\frac{t_1}{t_2} = \frac{G_s(G_r + G_s)}{G_r \cdot G_s} = \frac{G_r + G_s}{G_r}$$

which by rearrangement gives:

$$G_s/G_r = t_1 - t_2/t_2$$

Definitions:
$G_s$ = Conductivity of sample to be determined
$G_r$ = Conductivity of a reference
$G_{ser}$ = Conductivity of the reference and sample combined together in a series manner = $G_rG_s/(G_r + G_s)$
K = A constant of proportionality which is deemed to apply equally to both $t_1$ and $t_2$ as described above.
$t_1$ = Time period taken to charge capacitor C1 from a lower voltage limit to an upper voltage limit.
$t_2$ = Time period taken to discharge the same capacitor C1, between the same limits of voltage.
$V_s$ = Suitable supply potential for circuit.

$\left.\begin{array}{l}V_1 \\ V_2\end{array}\right\}$ = Upper and lower limits of potential across capacitor C1 used for determining portions of the cycle.

C1 = Capacitance value of capacitor used.

By using well-known circuit techniques, analogue quantities or digital counts may be obtained which are in proportion to $G_r$ and $G_s$ respectively enabling the circuit to give useful outputs to indicating or other devices and circuits.

It is shown that long term changes in the value of C1, supply voltage and many other circuit parameters have little or no effect on the circuit performance.

Ultimately, the ratio of $G_s$ to $G_r$ obtained by such a circuit is shown to be dependent on the stability of $G_r$ alone.

It will be seen that from the foregoing there is a considerable advantage in that an extremely neat and simple conductivity measuring device is provided which can be reduced to small proportions by using a small battery supply and the device is of particular value, for example, in testing the conductivity of separate quarters of a cow to test for mastitis. Thus, the display device may be operated to give a reading for each quarter, the conductivity cell being emptied of the milk from that first quarter, refilled for the next, emptied again and so on and the micro-processor for example, an 8048 microprocessor may be programmed so that the levels of conductivity from the various quarters may be compared with each other and, if necessary, with a standard conductivity to give indications as to whether there is a positive or negative indication of presence of mastitis in any one or more quarters of the animal together with an indication on the display of the quarter which is affected. The arrangement has the particular advantage however that the stability and accuracy depend solely on the stability and accuracy of the conductance $G_r$ and accordingly very accurate readings can be given.

I claim:

1. Apparatus for use in a device for indicating the electrical conductivity of liquid in an electrical conductivity cell having a pair of terminals, said apparatus comprising:
    an oscillator having a resistance-capacitance network which includes said cell;
    a capacitor;
    an electronic device which has different conducting states in response to application of high potential and low potential, respectively, being applied thereto;
    a reference conductance;
    an electrical potential source;
    means for applying a potential from said source to the terminals of said cell by applying the potential to said capacitor, said cell, and said reference conductance such that current is cyclically reversed in said cell;
    whereby the time period of the cyclical reversal of current in said cell is an indication of the conductivity of the liquid in the cell in terms of the conductivity of the reference conductance.

2. Apparatus for use in indicating the electrical conductivity of a liquid in an electrical conductivity cell having a pair of terminals wherein said liquid is disposed in series between said terminals, said apparatus comprising:
    an oscillator having a resistance-capacitance network which includes said cell;
    a capacitor connected in series with said oscillator;
    an electronic device having sensing leads connected in series with said capacitor, said electronic device having different conductance conditions in response to application of high potential and low potential, respectively, across said sensing leads;
    a reference conductance;
    a source of electrical potential;
    means for applying potential from said source to said resistance-capacitance network to charge said capacitor through said cell until the increase in potential resulting from such charge causes said electronic device to change its conductance condition to permit the capacitor to discharge through said cell and reduce the potential applied to said capacitor, thereby causing the electronic device to again change its conductance condition, thereby completing an operating cycle;
    whereby the time period of said operating cycle is proportional to the conductivity of said liquid.

3. In a method of measuring the electrical conductivity of liquid in a conductivity cell, the steps of:
    (a) passing current in a first direction through said conductivity cell and through a capacitor connected in series with said conductivity cell until a first predetermined voltage appears across said capacitor;
    (b) in response to said first predetermined voltage appearing across said capacitor, passing current in a second direction, opposite said first direction, through said conductivity cell and said capacitor until the voltage across the capacitor reaches a second predetermined level;
    (c) in response to the voltage across said capacitor reaching said second predetermined level, repeating steps (a) and (b) cyclically;
    whereby the times required for the voltage across the capacitor to reach said first and second predetermined levels depends upon the conductance of said conductivity cell.

* * * * *